United States Patent [19]

Laruelle et al.

[11] Patent Number: 4,794,121
[45] Date of Patent: Dec. 27, 1988

[54] ALKYLCARBOXAMIDES OF PYRIDYLALKYLAMINES, AND THEIR USE IN HUMAN AND VETERINARY MEDICINE

[75] Inventors: Claude Laruelle, Villeneuve Loubet; Marcel Lepant, Nice; Bernard Raynier, Cagnes, all of France

[73] Assignee: Panmedica, Carros, France

[21] Appl. No.: 908,680

[22] Filed: Sep. 18, 1986

[30] Foreign Application Priority Data

Oct. 11, 1985 [MA] Morocco ................................. 20776

[51] Int. Cl.$^4$ .................... C07D 213/56; A61K 31/44
[52] U.S. Cl. ..................................... 514/357; 546/336; 546/337
[58] Field of Search ................. 546/336, 337; 514/357

[56] References Cited

U.S. PATENT DOCUMENTS 4,452,983 1/1984 Johnson et al. ................. 546/233

FOREIGN PATENT DOCUMENTS 0101380 4/1984 European Pat. Off. ........... 546/337

*Primary Examiner*—Mary C. Lee
*Assistant Examiner*—J. Richter
*Attorney, Agent, or Firm*—Browdy and Neimark

[57] ABSTRACT

Alkylcarboxamides of pyridylalkylamines, useful in human and verterinary medicine, correspond to the general formula I:

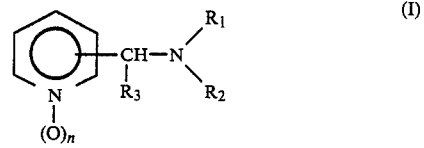

wherein
n=0 or 1,
$R_3$ represents an alkyl group of $C_1$ to $C_3$ or a hydrogen atom,
$R_1$ represents a hydrogen atom,
$R_2$ represents a group:

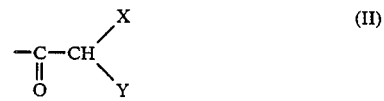

in which:
X and Y are different,
X and Y each represent a linear or branched saturated or unsaturated hydrocarbon chain comprising from 1 to 16 carbon atoms;
X and Y together determine a saturated or unsaturated cyclic radical substituted or not comprising from 3 to 12 carbon atoms.

16 Claims, No Drawings

ALKYLCARBOXAMIDES OF PYRIDYLALKYLAMINES, AND THEIR USE IN HUMAN AND VETERINARY MEDICINE

BACKGROUND OF THE INVENTION

The present invention relates to novel aliphatic and cycloaliphatic amides of pyridylalkylamines or their N-oxide derivatives of the general formula:

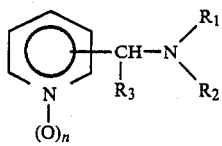

in which:

$n = 0$ or $1$, $R_3$ represents an alkyl group of $C_1$ to $C_3$ or a hydrogen atom, $R_1$ represents a hydrogen atom, $R_2$ represents a group:

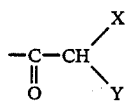

in which:

X and Y are different,

X and Y each represent a linear or branched saturated or unsaturated hydrocarbon chain comprising from 1 to 16 carbon atoms;

X and Y together determine a saturated or unsaturated cyclic radical subsistuted or not comprising from 3 to 12 carbon atoms.

The compounds according to the present invention have particularly interesting pharmacological properties, namely parasympathomimetic, hypertensive, bradycardiac, antianoxic, analgesic, antispasmodic and broncholytic.

SANOFI in its patent E.P. 101,380 described the nicotinic amide of picolylamine. Later, Riker in U.S. Pat. No. 4,452,983 claimed picolinic 2-trifluoro 2-ethoxy 5-hydroxy benzamide.

Benoit-Guyod in Chimie Therapeutique (1968)-336 studied the activities of the amides of dipropylacetic acid and noted the absence of anticonvulsant properties of the series.

Applicant has discovered surprisingly that the amides according to the general formula I possessed the previously mentioned pharmacological activities and could constitute particularly interesting medicaments.

GENERAL DESCRIPTION OF THE INVENTION

According to the invention there are provided compounds of the general formula I or one of its pharmaceutically acceptable salts.

The present invention also relates to the process of the preparation of the derivatives of the general formula I. The process consists of reacting a pyridylalkylamine with a reactive derivative of the general formula (III):

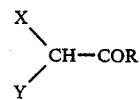

This reactive derivative may be a halogenide (R=halogen) or an acid anhydride, a reactive ester or a mixed anhydride.

Among the acid halogenides it is the chloride which is used preferably; it is mostly available or can be prepared in customary manner. In this case, the reaction is normally performed with pyridylmethanamine in an inert solvent such as benzene, toluene ether or a halogenalkane.

A hydrogen acceptor is used which can be tertiary amines such as triethylamine, pyridine, picoline or again an excess of the pyridylmethanamine which is then recovered in the form of the hydrochloride. The reaction temperatures may be comprised between ordinary temperature and the reflux temperature of the reaction medium. The highest reaction temperatures may be employed with the least reactive derivatives of formula III.

Other derivatives of the general formula III may be used, like esters such as the pentachlorophenyl ester, in which case the operation is at ambiant temperature and in an inert polar solvent such as dimethylformamide preferably at ordinary temperature.

It is also possible to use a mixed anhydride such as a reactive derivative of the general formula (III) carried out, for example, with pivaloyl chloride or ethylchloroformate in the presence of a tertiary amine like triethylamine in solution in acetone.

It is also possible to react the carboxylic acid general formula III (R=OH) with pyridinemethanamine in the presence of a dehydrating catalyst like a carbodiimide, for example, dicyclohexylcarbodiimide in solution in dimethylformamide or in an inert chlorinated solvent, at ordinary temperature.

According to a particular modality of the present invention, it is possible to carry out the reaction of the acid chloride of formula III (R=Cl) in solution in chloroform with the equimolecular amount of pyridinemethanamine. The basic amide formed remaining in solution in the solvent then serves as hydrochloric acid acceptor and it is possible to recover from the chloroform solution, after filtration of traces of insoluble pyridinemethanamine chloride, the derivatives of the present invention.

It is also possible to take up again in water the residue from evaporation of the chloroform and to obtain the base in the pure state after alkalinisation by an inorganic base. The amides thus isolated may be salified with pharmaceutically acceptable inorganic or organic acids.

The N-oxide derivatives of general formula I may be prepared from the amides of pyridinemethanamine by the action of hydrogen peroxide in solution in acetic acid.

The temperature of the reaction medium can be regulated between ordinary temperature and reflux temperature preferably between 60° and 100° C.

The isolation of the desired N-oxide derivatives is done by evaporation of the acetic acid under reduced pressure, extraction by a water immiscible solvent, washing with dilute caustic soda and evaporation.

The taking up of the evaporate with ether results in the N-oxide derivatives of the present application in the pure state. The products according to the invention are pure by thin layer chromatography in the solvent systems indicated and their elementary analysis corresponds to the calculated theoretical results.

The present application relates also to a pharmaceutical composition comprising at least one derivative of the general formula I in the state of base or in one of its pharmaceutically acceptable salts. These compositions may be prepared for the purpose of oral or parenteral administration with the adjuvants generally employed. The administration can also be performed by suppository or percutaneous preparation with suitably selected vectors.

PHARMACOLOGICAL STUDY (1) Potentiation of the hypnotic action of pentobarbital The derivatives according to the invention are injected intraperitoneally into mice, then after 30 min., 50 mg/kg of pentobarbital i.p. A very significant potentiation of narcosis for doses comprises between 6 and 24 mg/kg is noted.

(2) Analgesic activity

By administration to the mouse of the derivatives at the dose of 6, 12, 24 mg/kg, there is noted in the acetic acid test a very significant analgesic action from 12 mg/kg.

In the heated plate test, this activity is noted from 6 mg/kg by the intraperitoneal route and at 24 mg/kg by the oral route.

No analgesic response with respect to electric stimulation is noted at the doses employed.

(3) Antispasmodic activity

Tested on the rabbit jejunum and on the guinea pig ileum, the derivatives according to the invention exert an antagonistic effect with respect to histamine varying from 10 to 50% for concentrations in the medium of 1 to $2 \times 10^{-2}$ μg/ml.

The spasmolitic action is confirmed for certain derivatives on the isolated uterus.

(4) Bronchodilator activity

A protective effect with respect to histamine bronchospasm is noted in the anesthetized animal from the dose of 20 mg/kg for certain derivatives of the present application. In acetylcholine spasm, the derivative of Example 7 administered at 50 mg/kg by mouth exerts a bronchial protection of 100%.

(5) Antianoxic activity

The derivatives according to the invention also protect against experimental hypoxia in the mouse.

In curare anoxia (Flaxedyl at 16 mg/kg), a delay in the convulsive crisis of 30 to 50% is noted particularly with the derivatives of examples 5, 7, 11, 16, after intraperitoneal administration at the dose of 100 mg/kg. The anticurarizaring effect is sufficient for certain animals to survive the convulsive crisis.

In the test of anoxia by confinement; the products claimed increase the survival level up to 60% in some cases.

(6) Anticonvulsant activity

The derivatives according to the invention do not protect the mouse in the convulsive crisis caused by pentetrazole.

Some non-limiting examples of the present application are described below.

EXAMPLE 1

N-(3-PYRIDYL METHYL)-CYCLOHEPTANE-CARBOXAMIDE HYDROCHLORIDE

In one hour at ordinary temperature 0.1 mole of picolylamine in solution in 30 ml of chloroform are run into 0.11 mole of cycloheptane carboxylic acid chloride dissolved in 75 ml chloroform.

It is kept at ordinary temperature with stirring for 24 hours, a light and soluble product constituted by the amine hydrochloride is filtered off if nessessary, and it is evaporated to dryness. The residue taken up again in water is treated with aqueous caustic soda to pH 10 and extracted with choloroform.

After washings with water of the organic layer and evaporation, the crude product is recrystallized in a benzene/cyclohexane mixture. In this way the derivative of the title is obtained in the form of the base with a yield of 80% in the form of a white solid of m.p. 65°/66° C. showing in thin layer chromatography on silica a single spot of Rf 0.95 in the system A: ethyl acetate 2, isopropanol 2, concentrated ammonia 1 and Rf=0.60 in the system B: benzene 80, methanol 20.

By treatment of the acetone solution of this base with hydrochloric acid, the hydrochloride is isolated, i.e. the title derivative, in the form of white crystals of m.p. 83°/85° C.

By operating under the conditions of Example 1 with the corresponding acid chlorides, the derivatives of the formula:

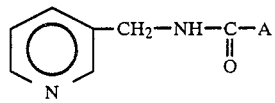

are obtained, having the following physico-chemical characteristics:

| A | | Yield | m.p. base | m.p. HCl | Rf in A | Rf in B |
|---|---|---|---|---|---|---|
| Ex 2 | cyclohexyl | 82% | 98/99 | 79/80 | 0.95 | 0.50 |
| Ex 3 | cyclooctyl | 67% | oil | 87 | 0.95 | 0.50 |
| Ex 4 | cyclopentyl | 75% | 71 | 117 | 0.95 | 0.50 |
| Ex 5 | t-butyl | 70% | 70 | 178/79 | 0.95 | 0.55 |
| Ex 6 | cyclopropane | 83% | 129/130 | 181/183 | 0.95 | 0.59 |

| A | Yield | m.p. base | m.p. HCl | Rf in A | Rf in B |
|---|---|---|---|---|---|
| Ex 7 CH₃−CH₂−CH(CH₃)− | 80% | oil | 65 | 0.95 | 0.65 |
| Ex 8 CH₃−(CH₂)₃−CH(C₂H₅)− | 90% | 35/36 | 78/80 | 0.95 | 0.67 |

By operating under the conditions of example 1 and by using 2-pyridylmethanamine pyridylmethanamine with suitable acid chlorides, the derivatives of the formula:

$$\text{2-pyridyl-CH}_2\text{-NH-C(=O)-A}$$

are obtained, having the following physico-chemical characteristics:

| A | Yield | m.p. base | m.p. HCl | Rf in A | Rf in B |
|---|---|---|---|---|---|
| Ex 9 (cyclohexyl) | 85% | 95 | 135 | 0.90 | 0.60 |
| Ex 10 (cyclopentyl) | 65% | 65 | 130 | 0.90 | 0.60 |
| Ex 11 (cyclobutyl) | 70% | oil | 70 | 0.90 | 0.65 |
| Ex 12 CH₃−(CH₂)₃−CH(C₂H₅)− | 92% | 40 | 85/87 | 0.90 | 0.70 |
| Ex 13 (bicyclic) | 85% | 136/138 | 190 | 0.90 | 0.65 |

By operating under the conditions of Example 1 and by using 4-pyridylmethanamine and the corresponding acid chlorides, the derivatives of the general formula:

$$\text{4-pyridyl-CH}_2\text{-NH-C(=O)-A}$$

are obtained having the following physico-chemical characteristics:

| A | Yield | m.p. base | m.p. HCl | Rf in A | Rf in B |
|---|---|---|---|---|---|
| Ex 14 | 72% | 60 | 135 | 0.92 | 0.50 |
| Ex 15 | 80% | 80/85 | 100 | 0.92 | 0.50 |
| Ex 16 CH₃−(CH₂)₃−CH(C₂H₅)− | 85% | oil | 85/90 | 0.92 | 0.60 |

EXAMPLE 17

N₁ OXIDE OF N-(3-PYRIDYL METHYL) 2-ETHYL HEXANAMIDE 20 millimoles of N-(3-pyridyl methyl) 2-ethyl hexanamide base (Example 8) are dissolved in 50 ml of acetic acid then 10 ml of 40% hydrogen peroxide added. It is taken then for 3 hours to 80° and then on the water bath under vacuum the major part of the acetic acid is evaporated; it is taken up again with ice water and made alkaline at pH 10.5 with dilute sodium hydroxide. It is extracted with chloroform, washed with water and the solvent evaporated.

After taking up again with ether, the derivative of the title is obtained a yield of 61% in the form of white crystals of m.p. 107°/108° C. showing in TLC on silica a single spot of Rf=0.25 in the system B and of 0.45 in the system: n butanol 8, acetic acid 1, water 1. The IR spectrum recorded in KBr shows a band N→O at 1290 cm⁻¹.

EXAMPLE 18

N₁ OXIDE OF N-(3-PYRIDYL METHYL)CYCLOHEXANE CARBOXAMIDE

By operating under the conditions of the preceeding example from the N-(3-pyridyl methyl)cyclohexane carboxamide base described in Example 2, the title derivative is obtained in the form of white crystals of m.p. 90°/92° C., showing a simple spot in TLC in the system A of Rf=0.30 and a single spot of Rf 0.33 in the system n butanol 8, water 1, acetic acid 1. The I.R. spectrum recorded in KBr shows a band N→O at 1290 cm⁻¹.

We claim:

1. A compound of formula I or one of its pharmaceutically acceptable salts:

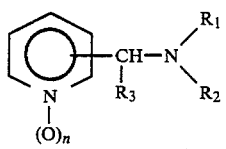

(I)

in which:
n=0 or 1,
R₁ represents a hydrogen atom,
R₃ represents an alkyl group of C₁ to C₃ or a hydrogen atom,
R₂ represents:

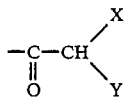
(II)

in which:
(1) X and Y are different and individually represent —(CH₂)m—CH₃, m being a number between 0 and 14; or
(2) X and Y together form an unsubstituted saturated cyclic hydrocarbon of from 3 to 12 carbon atoms or a cyclic saturated hydrocarbon of from 3 to 12 carbon atoms substituted by a methyl group.

2. A compound according to claim 1 in which the ring nitrogen of the pyridine is in a state of N oxide.

3. A compound according to claim 1 selected from the group consisting of
N-(3-pyridyl methyl)-cyclooctane carboxamide,
N-(3-pyridyl methyl)-cycloheptane carboxamide,
N-(3-pyridyl methyl)-cyclohexane carboxamide,
N-(3-pyridyl methyl)-cyclopentane carboxamide,
N-(3-pyridyl methyl)-cyclopropane carboxamide,
N-(3-pyridyl methyl) 2-ethyl hexanamide, and
N-(3-pyridyl methyl)-cyclododecane carboxamide.

4. A compound according to claim 1 selected from the group consisting of
N-(4-pyridyl methyl)-cyclopropane carboxamide,
N-(4-pyridyl methyl)-cyclohexane carboxamide, and
N-(4-pyridyl methyl) 2-ethyl hexanamide.

5. A compound according to claim 1 selected from the group consisting of
N-(2-pyridyl methyl)-cyclododecane carboxamide,
N-(2-pyridyl methyl)-cyclobutane carboxamide, and
N-(2-pyridyl methyl) 2-ethyl hexanamide.

6. A compound according to claim 1 selected from the group consisting of
N₁ oxide of N-(3-pyridyl methyl)-cyclohexane carboxamide and
N₁ oxide of N-(3-pyridyl methyl) 2-ethyl hexanamide.

7. A therapeutic method of treating a human or animal to produce para-sympathomimetic, anti-hypertensive, bradycardiac, antianoxic, analgesic, antispasmotic or broncholytic effects, comprising administering to the human or animal a compound of formula I or one of its pharmaceutically acceptable salts:

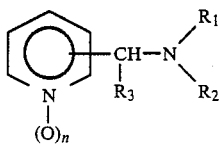
(I)

in which:
n=0 or 1,
R₁ represents a hydrogen atom,
R₃ represents an alkyl group of C₁ to C₃ or a hydrogen atom, R₂ represents:

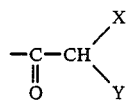
(II)

in which:
(1) X and Y are different and individually represent —(CH₂)m—CH₃, m being a number between 0 and 14; or
(2) X and Y together form an unsubstituted saturated cyclic hydrocarbon of from 3 to 12 carbon atoms or a cyclic saturated hydrocarbon of from 3-12 carbon atoms, in an amount therapeutically effective to produce at least one of said effects.

8. A method of treating hypertension in humans or animals according to claim 7 comprising administering an antihypertensive effective amount of said compound or salt to said human or animal.

9. A method of creating para-sympathomimetic effects in humans or animals according to claim 7 comprising administering a para-sympathomimetically effect amount of said compound or salt to said human or animal.

10. A method of treating producing bradycardiac effects in humans or animals according to claim 7, comprising administering a bradycardically effective amount of said compound or salt to said human or animal.

11. A method of treating anoxia in humans or animals according to claim 7, comprising administering an antianoxically effective amount of said compound or salt to said human or animal.

12. A method of analgesia according to claim 7, comprising administering an analgesically effective amount of said compound or salt to said human or animal.

13. A method of treating spasms according to claim 7, comprising administering an antispasmodically effective amount of said compound or salt to said human or animal.

14. A method of producing broncholytic activity in a human or animal according to claim 7, comprising administering a broncholytically effective amount of said compound or salt to said human or animal.

15. A pharmaceutical composition for treating a human to produce para-sympathomimetic, antihypertensive, bradycardiac, antianoxic, analgesic, antispasmotic or broncholytic effects, comprising an amount of a compound according to claim 1 therapeutically effective to produce at least one of said effects, and a pharmaceutically acceptable vector or adjuvant.

16. The pharmaceutical composition for therapeutically treating a human to produce para-sympathomimetic, antihypertensive, bradycardiac, antianoxic, analgesic, anti-spasmotic or broncholytic effects comprising an amount of a compound according to claim 2 therapeutically effective to produce at least one of said effects, and a pharmaceutically acceptable vector or adjuvant.

* * * * *